United States Patent
van Hoeve et al.

(10) Patent No.: US 9,782,733 B2
(45) Date of Patent: Oct. 10, 2017

(54) APPARATUS AND METHOD FOR MASS PRODUCING A MONODISPERSE MICROBUBBLE AGENT

(75) Inventors: Willem van Hoeve, Enschede (NL); Elena de Castro Hernàndez, Sevilla (ES); José Manuel Gordillo Arias de Saavedra, Sevilla (ES); Andreas Michael Versluis, Enschede (NL); Detlef Lohse, Enschede (NL)

(73) Assignees: UNIVERSITEIT TWENTE, Enschede (NL); UNIVERSIDAD DE SEVILLA, Sevilla (ES)

( * ) Notice: Subject to any disclaimer, the term of this patent is extended or adjusted under 35 U.S.C. 154(b) by 122 days.

(21) Appl. No.: 14/386,318

(22) PCT Filed: Mar. 22, 2012

(86) PCT No.: PCT/NL2012/050179
§ 371 (c)(1),
(2), (4) Date: Dec. 26, 2014

(87) PCT Pub. No.: WO2013/141695
PCT Pub. Date: Sep. 26, 2013

(65) Prior Publication Data
US 2015/0125400 A1    May 7, 2015

(51) Int. Cl.
*B01F 5/06*    (2006.01)
*B01J 19/00*    (2006.01)
(Continued)

(52) U.S. Cl.
CPC .......... *B01F 5/0602* (2013.01); *A61K 49/223* (2013.01); *B01F 3/0446* (2013.01);
(Continued)

(58) Field of Classification Search
CPC .. B01F 5/0602; B01F 3/0446; B01F 3/04985; B01F 13/0062; B01F 13/0064;
(Continued)

(56) References Cited

U.S. PATENT DOCUMENTS

| | | | | |
|---|---|---|---|---|
| 6,467,331 B1 * | 10/2002 | Kline-Schoder | ......... | A61B 8/08 239/9 |
| 7,708,949 B2 * | 5/2010 | Stone | .................... | B01F 3/0807 422/110 |

(Continued)

FOREIGN PATENT DOCUMENTS

| | | |
|---|---|---|
| DE | 102 06 083 A1 | 2/2002 |
| WO | 2010/110843 A1 | 9/2010 |
| WO | WO 2013/001309 A2 | 1/2013 |

OTHER PUBLICATIONS

Castro-Hernández et al. "Microbubble generation in a co-flow device operated in a new regime", Lab Chip, 2011, 11, pp. 2023-2029.

(Continued)

*Primary Examiner* — Arthur O Hall
*Assistant Examiner* — Adam J Rogers
(74) *Attorney, Agent, or Firm* — Knobbe, Martens, Olson & Bear, LLP.

(57) ABSTRACT

An apparatus for mass producing monodisperse microbubbles contains a microfluidic flow focusing device. The microfluidic flow focusing device includes a dispersed phase fluid supply channel having an outlet that discharges into a flow focusing junction, a continuous phase fluid supply channel having an outlet that discharges into the flow focusing junction, and a bubble formation channel having an inlet disposed at the flow focusing junction. The configuration of the flow focusing junction is such that, in operation, a flow of dispersed phase fluid discharging from the outlet of the dispersed phase fluid supply channel is engageable in (Continued)

co-flow by a focusing flow of continuous phase fluid discharging from the outlet of the at least one continuous phase fluid supply channel under formation of a gradually thinning jet of dispersed phase fluid that extends into the inlet of the bubble formation channel.

21 Claims, 5 Drawing Sheets

(51) Int. Cl.
*B01F 13/00* (2006.01)
*B01F 3/04* (2006.01)
*A61K 49/22* (2006.01)
*B01F 5/00* (2006.01)

(52) U.S. Cl.
CPC ...... *B01F 3/04985* (2013.01); *B01F 13/0062* (2013.01); *B01F 13/0064* (2013.01); *B01F 13/0084* (2013.01); *B01F 13/0086* (2013.01); *B01J 19/0093* (2013.01); *B01F 2003/04858* (2013.01); *B01F 2005/0097* (2013.01); *B01F 2215/0034* (2013.01); *B01J 2219/0084* (2013.01); *B01J 2219/0086* (2013.01); *B01J 2219/00894* (2013.01); *B01J 2219/00959* (2013.01); *B01J 2219/00995* (2013.01)

(58) Field of Classification Search
CPC .............. B01F 13/0084; B01F 13/0086; B01F 2003/04858; B01F 2005/0097; B01F 2215/0034; A61K 49/223; B01J 19/0093; B01J 2219/0084; B01J 2219/0086
USPC ....................................................... 239/589.1
See application file for complete search history.

(56) References Cited

U.S. PATENT DOCUMENTS

| | | | |
|---|---|---|---|
| 7,776,927 B2* | 8/2010 | Chu | A61K 9/113 347/55 |
| 8,500,104 B2* | 8/2013 | Spears | B01F 3/0446 239/9 |
| 9,038,919 B2* | 5/2015 | Link | B01F 5/0682 239/10 |
| 9,039,273 B2* | 5/2015 | Weitz | A61K 9/113 366/175.2 |
| 2002/0185550 A1* | 12/2002 | Ganan-Calvo | A61M 15/0065 239/290 |
| 2007/0119987 A1* | 5/2007 | Vion | B03D 1/14 239/499 |
| 2007/0189972 A1* | 8/2007 | Chiba | A61K 49/223 424/9.52 |
| 2010/0027372 A1 | 2/2010 | Ozawa et al. | |
| 2010/0237163 A1* | 9/2010 | Chomas | B01F 5/0682 239/8 |
| 2011/0223314 A1 | 9/2011 | Zhang et al. | |

OTHER PUBLICATIONS

Desportes, et al. "Fluorescence lifetime imaging microscopy for in situ observation of the nanocrystallization of rubrene in a microfluidic set-up", Chemical Physics Letters 446, 2007, pp. 212-216.
Hardt et al. "Passive micromixers for applications in the microreactor and µTAS fields", Microfluid Nanofluid 1, 2005, pp. 108-118.
Park et al. "Achieving Uniform Mixing in a Microfluidic Device: Hydrodynamic Focusing Prior to Mixing", Anal. Chem. 78, 2006,. pp. 4465-4473.
Van Hoeve et al., "Microbubble formation and pinch-off scaling exponent in flow-focusing devices", Physics of Fluids 23, 2011, pp. 092001-to 092001-8.
International Search Report dated Jan. 3, 2013 for PCT/NL2012/050179.
Examination Report, dated Apr. 4, 2017, in European Application No. 12 713 394.0.
Tan Y.C., et al., Monodispersed Microfluidic Droplet Generation by Shear Focusing Microfluidic Devise, Sensors and Actuators B, vol. 114, No. 1, pp. 350-356, Jul. 26, 2005.

* cited by examiner

APPARATUS AND METHOD FOR MASS PRODUCING A MONODISPERSE MICROBUBBLE AGENT

This application is a U.S. National Phase of International Application No. PCT/NL2012/050179, filed Mar. 22, 2012, designating the U.S. and published in English as WO 2013/141695 on Sep. 26, 2013.

FIELD OF THE INVENTION

The present invention relates to the field of microfluidics, and more in particular to an apparatus and a method for the mass production of monodisperse microbubbles.

BACKGROUND

Microbubble production is an area of growing interest due to its countless applications in food processing, material science, pharmacy and medicine. In the field of medicine, for instance, microbubbles are used as contrast agent for medical ultrasound imaging, and as carriers for targeted drug delivery. Microbubbles for such therapeutic applications may preferably have a diameter in the range of 1-10 µm. Bubbles with larger diameters may not safely flow through the smallest capillaries of a patient's blood vessel system and provoke edema. Smaller bubbles may possess poor ultrasound reflectivity, or be inefficient as drug carriers.

Microbubbles with diameters in the desired range may be produced by either sonication or mechanical agitation. These methods, however, are only capable of generating colloids of polydisperse gaseous microbubbles within a liquid. The polydispersity of the microbubbles limits their potential use in therapeutic purposes. In ultrasound imaging applications, for example, monodispersity is required to provide an ultrasound image of sufficient quality; in drug transport applications, monodispersity is necessary to precisely control the amount of the drug to be delivered to the patient.

SUMMARY OF THE INVENTION

It is therefore an object of the present invention to provide for an apparatus and a method that enable the mass production of monodisperse microbubbles with controllable diameters below 10 µm, and preferably in the range of 2-5 µm.

The term 'monodisperse', where used in this text to characterize a collection of microbubbles, may be construed to mean that the polydispersity index (PDI) of the collection, mathematically defined as PDI=$s/r_b$, wherein $r_b$ denotes the average bubble radius and s the standard deviation of the bubble radii, is smaller than $5 \cdot 10^{-2}$. That is, a collection of bubbles having a PDI<5% may be considered to be monodisperse.

To this end, a first aspect of the present invention is directed to an apparatus for mass producing monodisperse microbubbles. The apparatus may comprise at least one microfluidic flow focusing device including a dispersed phase fluid supply channel having an outlet that discharges into a flow focusing junction; at least one continuous phase fluid supply channel having an outlet that discharges into the flow focusing junction; and a bubble formation channel having an inlet disposed at the flow focusing junction. The configuration of the flow focusing junction may be such that, in operation, a flow of dispersed phase fluid discharging from the outlet of the dispersed phase fluid supply channel is engageable in co-flow by a focusing flow of continuous phase fluid discharging from the outlet of the at least one continuous phase fluid supply channel under formation of a gradually thinning jet of dispersed phase fluid that extends into the inlet of the bubble formation channel. The bubble formation channel may have a length $L_{bfc}$ and a hydraulic diameter $D_{bfc}$, wherein $L_{bfc}/D_{bfc} \gg 1$.

A second aspect of the present invention is directed to a method of mass producing monodisperse microbubbles. The method may include providing an apparatus according to the first aspect of the invention. The method may also include supplying a flow of dispersed phase fluid through the outlet of the dispersed phase fluid supply channel into the flow focusing junction, and supplying a flow of continuous phase fluid through the outlet of the at least one continuous phase fluid supply channel into the flow focusing junction, such that, at the junction, the flow of dispersed phase fluid is engaged in co-flow by the focusing flow of continuous phase fluid under formation of a gradually thinning jet of dispersed phase fluid that extends into the inlet of the bubble formation channel, and monodisperse microbubbles, having a diameter smaller than the hydraulic diameter of the bubble formation channel break off a tip of said jet.

A third aspect of the present invention is directed to an agent, for instance a contrast agent for use in ultrasound imaging, including a plurality of monodisperse microbubbles manufactured by means of the apparatus according to the first aspect of the invention, and/or through the method according to the second aspect of the invention.

The apparatus according to the first aspect of the present invention is structurally simple and may be manufactured very economically, if desired as a disposable device. It enables the mass production of microbubbles with an extremely narrow size distribution and accurately controlled diameter well below 10 µm, e.g. in the range of 2-5 µm, in particular through the method according to the second aspect of the present invention. Microbubbles may be produced fast, at rates above $10^5$ microbubbles per second per microbubble-generating jet. In one embodiment, the apparatus may include multiple microfluidic flow focusing devices that may operate in parallel to boost the overall microbubble production rate further. The agent according to the third aspect of the present invention, comprising stable (optionally surfactant encapsulated), monodisperse microbubbles, may thus be produced rapidly in a single step, and in particular without any size-sorting steps that may be necessary with some conventional bubble production methods to obtain a monodisperse distribution.

These and other features and advantages of the invention will be more fully understood from the following detailed description of certain embodiments of the invention, taken together with the accompanying drawings, which are meant to illustrate and not to limit the invention.

DETAILED DESCRIPTION

Figure 1:
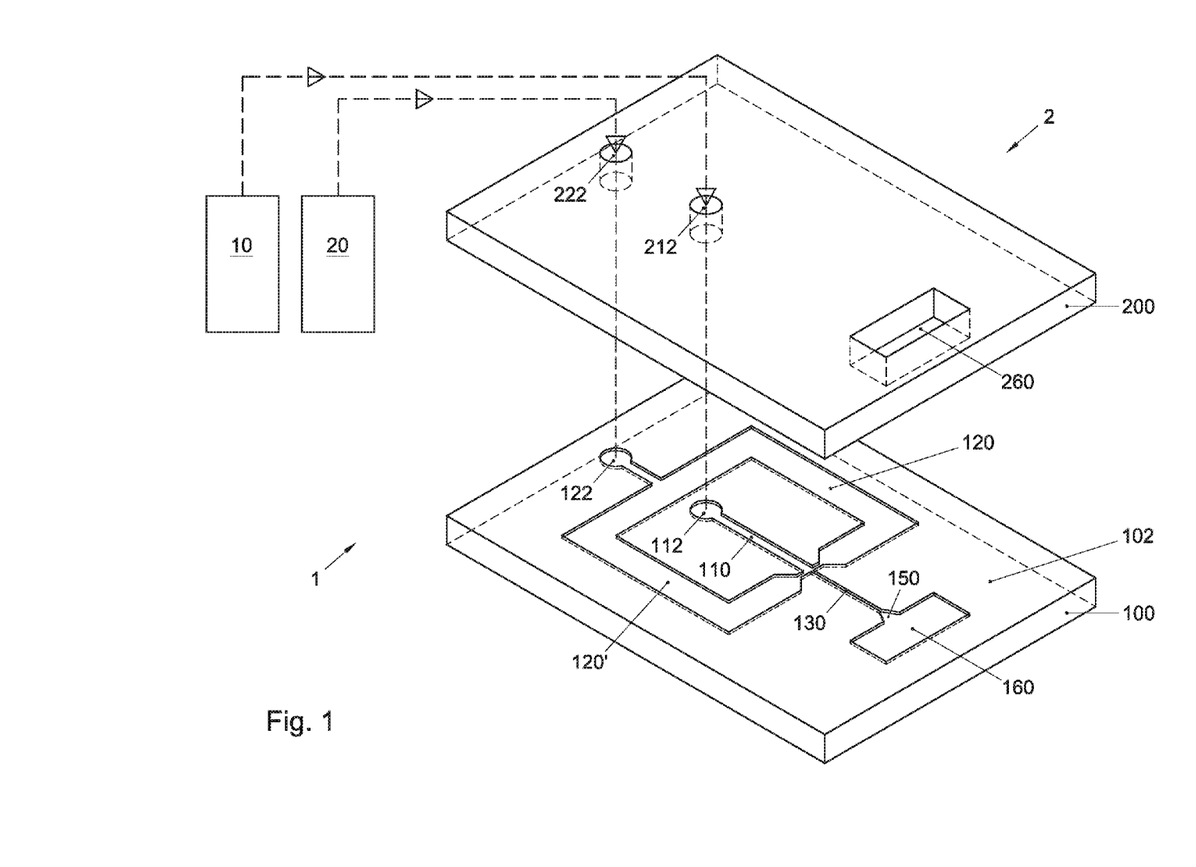
FIG. 1 shows a schematic perspective view of an exemplary embodiment of an apparatus according to the present invention.
Figure 2A:
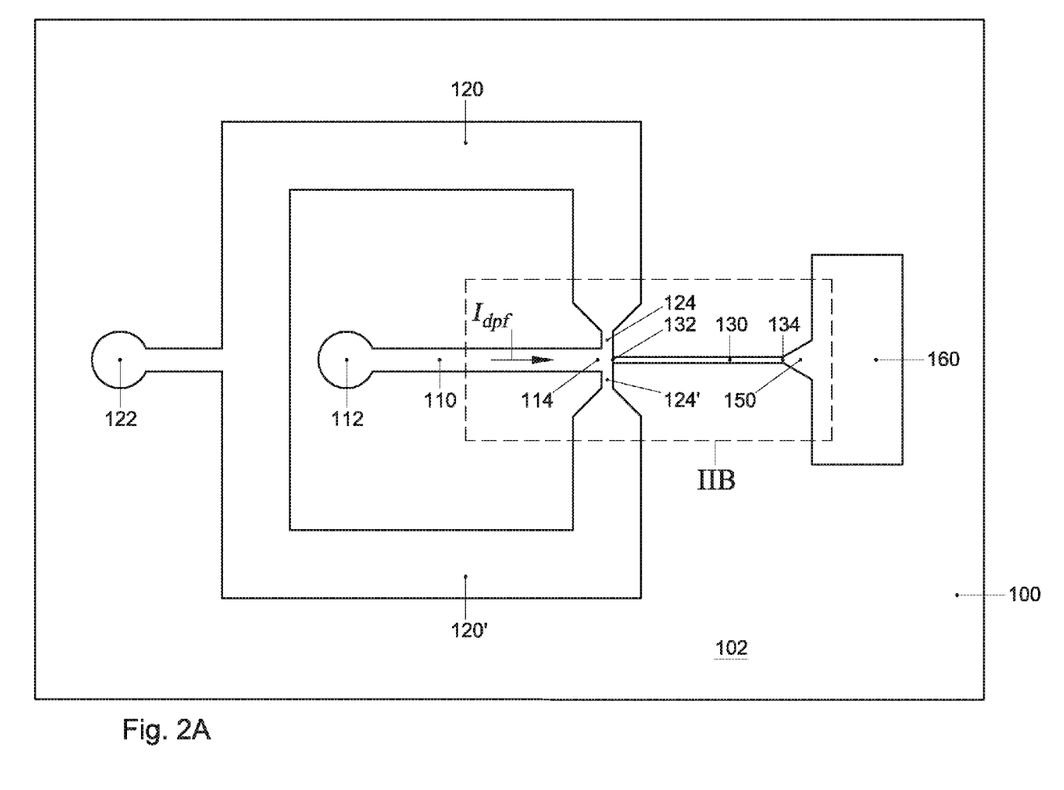
FIGS. 2A-B show a schematic top view of the base body of the microfluidic flow focusing device of the apparatus shown in FIG. 1.
Figure 2B:
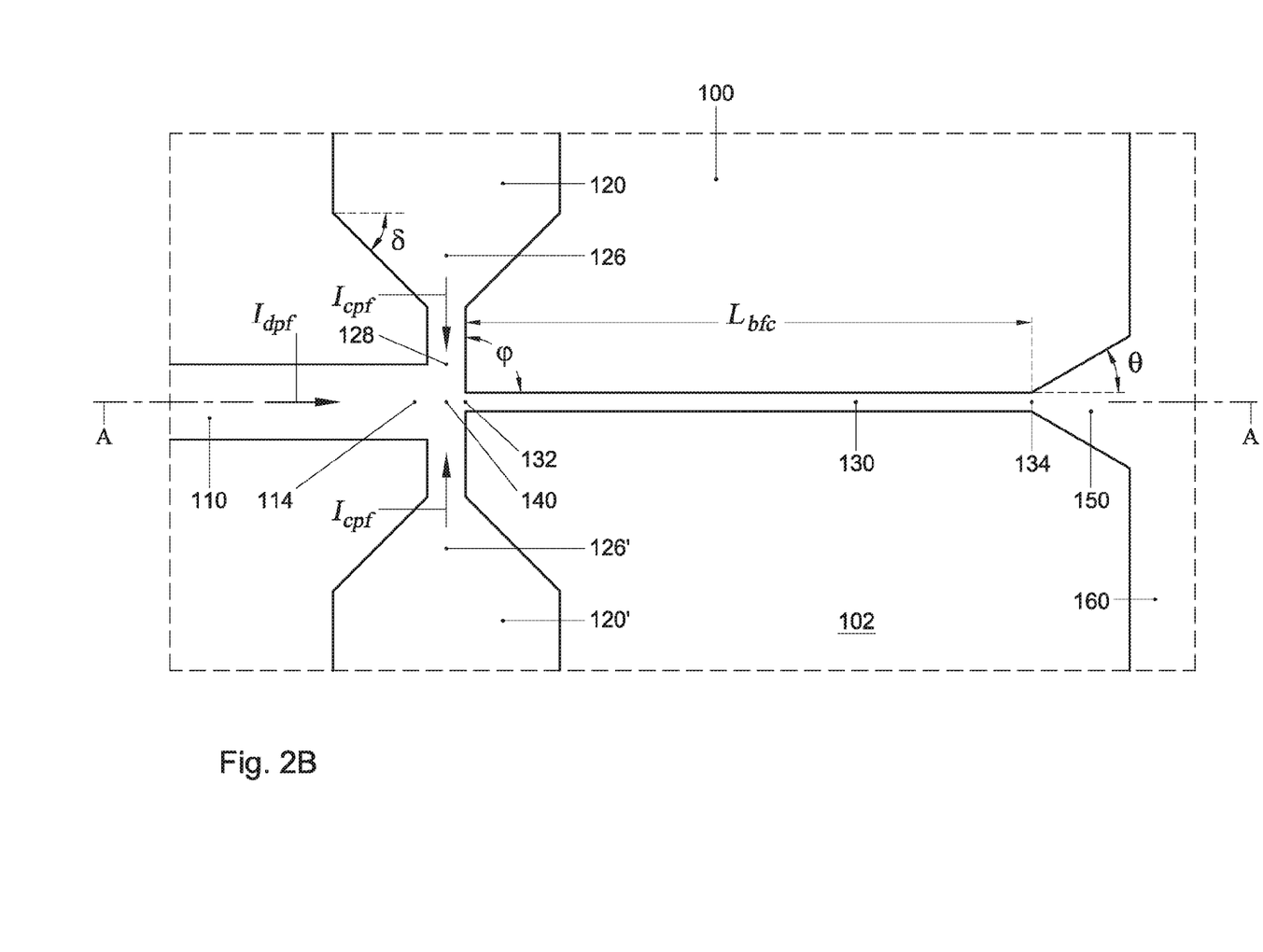

FIG. 1 shows a schematic perspective view of an exemplary embodiment of a microbubble mass production apparatus 1 according to the present invention. The apparatus 1 may include at least one microfluidic flow focusing device 2, a source of dispersed phase fluid 10 and a source of continuous phase fluid 20. The flow focusing device 2 may comprise two generally planar bodies, a base body 100 and a cover body 200, which, in an assembled condition of the flow focusing device 2, may be attached to one another, such that the structures indicated with reference numbers 112, 122 and 160 in the base body 100 are in registry with respective, geometrically corresponding passages through the cover body 200 labelled 212, 222 and 260. FIG. 2 shows a schematic top view of the base body 100.

Referring now to in particular FIGS. 1 and 2A-B to illustrate the construction of the apparatus 1.

The generally plate-shaped base body 100 may include a main surface 102 defining a planar arrangement of open-top surface channels; in an assembled condition of the flow focusing device 2, the flat, lower main surface 204 of the cover body 200 may close the top-side of the channels, so as to fully define them. The arrangement of channels may include a dispersed phase fluid supply channel 110, at least one continuous phase fluid supply channel 120, 120', and a bubble formation channel 130. The channels 110, 120, 120', 130 of the arrangement may join one another at a flow focusing junction 140.

Each of the channels 110, 120, 120', 130 may be a microchannel, i.e. a channel having a hydraulic diameter that is preferably smaller than 1 mm, or at least smaller than 10 mm. In the depicted embodiment all channels 110, 120, 120', 130 have a depth of 50 µm (measured perpendicular to the main surface 102 of the base body 100), while the widths of the respective channels (measured parallel to the main surface 102 of the base body 100) differ, ranging from several tens to several hundreds of micrometers. The transverse cross-sectional shape of each of the channels 110, 120, 120', 130 in the depicted embodiment is rectangular. It is contemplated, however, that the channels in different embodiments may have different dimensions, e.g. a different depths and widths, and that their transverse cross-sectional shapes may be different, e.g. otherwise polygonal or circular.

The dispersed phase fluid supply channel 110 may extend from an inlet 112, which may be fluidly connected to the source of dispersed phase fluid 10, to an outlet 114 that discharges into the flow focusing junction 140. The dispersed phase fluid supply channel 110 may preferably be straight, and at least its outlet 114 may extend in a dispersed phase fluid jet direction $I_{dpf}$. A hydraulic diameter of the dispersed phase fluid supply channel 100, $D_{dpf}$, may preferably be substantially uniform over its length, and be in the range of about 40-120 µm; in the depicted embodiment the dispersed phase fluid supply channel 100 has a uniform width of 200 µm.

The two continuous phase fluid supply channels 120, 120' may extend from a common inlet 122, which may be fluidly connected to a source of continuous phase fluid 20, to respective outlets 124, 124' that discharge into the flow focusing junction 140. At least the outlets 124, 124' of the continuous phase fluid supply channels 120, 120' may extend in respective continuous phase fluid discharge directions $I_{cpf}$, $I_{cpf}'$. The outlets 124, 124' may further have a substantially identical geometry, and be disposed symmetrically opposite to each other with respect to a central axis A of the dispersed phase fluid supply channel 110, such that their respective continuous phase fluid discharge directions $I_{cpf}$, $I_{cpf}'$ are aligned/in parallel and extend substantially perpendicular to the dispersed phase fluid jet direction $I_{dpf}$. Upstream of their respective outlets 124, 124', the continuous phase fluid supply channels 120, 120' may preferably have a relatively large hydraulic diameter $D_{cpfsc}$, e.g. $D_{cpfsc} \gg 90$ µm, so as to ensure little resistance in the supply of continuous phase fluid 22, and to warrant stable dispersed phase fluid-continuous phase fluid interfaces 30 at the flow focusing junction 140 during operation (see FIG. 4). Just upstream of their outlets 124, 124' the continuous phase fluid supply channels 120, 120' may include a tapering portion 126, 126' that tapers off in the downstream directions (δ~45°), causing their hydraulic diameters to gradually decrease up to a hydraulic diameter $D_{cpfsc,outlet} < D_{cpfsc}$. The opposing, aligned outlets 124, 124' may thus define a cross-channel 128 with a hydraulic diameter $D_{cpfsc,outlet}$, that, as part of the flow focusing junction 140, joins at right angles with the outlet 114 of the dispersed phase fluid supply channel 110. $D_{cpfsc,outlet}$ may preferably be in the range of about 50-80 µm. In the depicted embodiment, upstream portions of the continuous phase fluid supply channels 120, 120' have a width of about 600 µm, while at their outlets 124, 124', their width is approximately 100 µm.

The bubble formation channel 130 may extend from an inlet 132, which may be disposed at the flow focusing junction 140, to an outlet 134. The bubble formation channel 130 may preferably be straight, and have a hydraulic diameter $D_{bfc}$ that is smaller than the hydraulic diameter $D_{bfsc}$ of the dispersed phase fluid supply channel 110. At the same time, $D_{bfc}$ may preferably be significantly greater, e.g. about one order of magnitude, than a diameter $d_b$ of the microbubbles 36 to be formed inside during operation, such that these bubbles 36 can be transported through the channel 130 without being squeezed between the walls thereof (see FIG. 4). This latter condition avoids clogging of the bubble formation channel 130 with bubbles 36, but is also of general importance to the bubble formation process, as will be clarified below. In a preferred embodiment $D_{bfsc}$ may preferably be in the range of 10-100 µm, and more preferably in the range of 25-75 µm. In the depicted embodiment, the bubble formation channel 130 has a square transverse cross-section, with a width $w_{bfc}$ and $D_{bfc}$ of 50 µm. Furthermore, the bubble formation channel 130 may preferably have a length $L_{bfc}$ that is much greater than its hydraulic diameter, i.e. $L_{bfc} \gg D_{bfc}$; in the depicted embodiment, for instance, $L_{bfc}$ is 1500 µm, such that $L_{bfc}/D_{bfc} = 30$. The relatively great length $L_{bfc}$ of the bubble formation channel 130 ensures that the (laminar) flow of continuous phase fluid 22 that is forced through the bubble formation channel 130 during operation is enabled to develop an at least approximately parabolic velocity profile. Full development is not necessary, but may be desirable. As will be elucidated in some more detail below, the development of the flow of continuous phase fluid is important to the optimal functioning of the apparatus 1. The inlet of the bubble formation channel 132 may be disposed opposite the outlet of the dispersed phase fluid supply channel 114, across the cross-channel 128 defined by the outlets 124, 14' of the continuous phase fluid supply channels 120, 120', such that a central axis of the bubble formation channel 130 is aligned with a central axis A of the dispersed phase fluid supply channel 110, and extends in the dispersed phase fluid jet direction $I_{dpf}$. At the point where the inlet 132 of the bubble formation channel 130 connects to the flow focusing junction 140, and more specifically to the cross-channel 128, the walls of the respective channels 128, 130 may meet at approximately right angles to define an inlet angle φ~90° that maximizes a continuous phase fluid pressure gradient along the bubble formation channel 130 during operation.

Accordingly, the flow focusing junction 140 defined by the four channels 110, 120', 120', 130 may preferably be substantially symmetrical relative to the central axis A of the bubble fluid supply channel 110, and hence to the dispersed phase fluid jet direction $I_{dpf}$. More specifically, the configuration of the flow focusing junction 140 may be such that, in operation, a flow of dispersed phase fluid 12 discharging from the outlet of the dispersed phase fluid supply channel 114 is engageable in co-flow by a flow of continuous phase fluid 22 discharging from the outlets 124, 124' of the continuous phase fluid supply channels 120, 120' under formation of a gradually thinning jet 32 of dispersed phase fluid 12 that extends into the inlet 132 of the bubble formation channel 130 (see FIG. 4).

Figure 4:
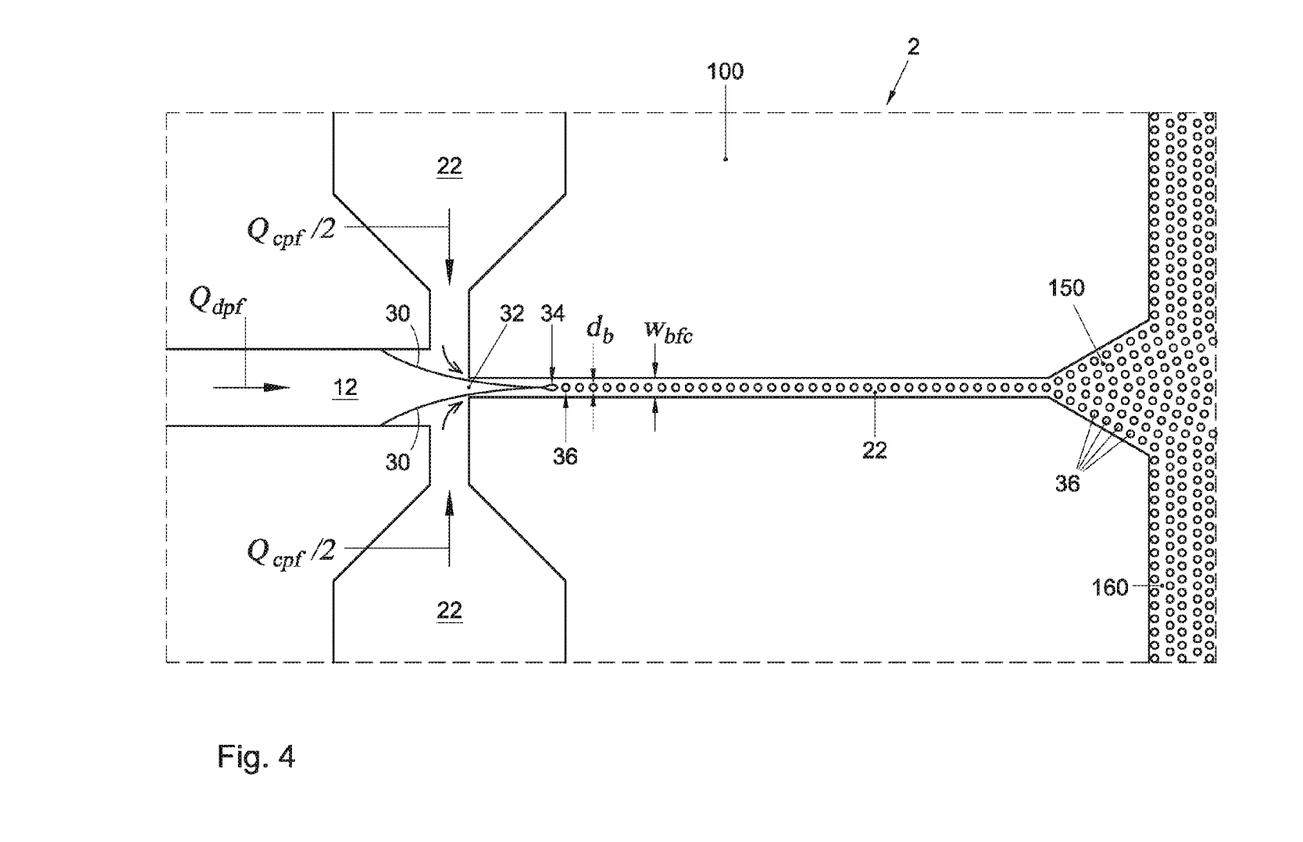
FIG. 4 shows a schematic top view of the microfluidic flow focusing device of the apparatus in FIG. 1 in operation.

Inside the bubble formation channel 130, the jet 32 may be inherently unstable, as a result of which bubbles 36 may break or pinch off its tip 34. This is the principle bubble formation mechanism on which the apparatus 1 is based. However, as the dimensions of the bubbles 36 may be directly related to the dimensions of the tip of the jet 34, which thins as it extends further into the longitudinal direction, undesired early break up of the unstable tip 32 may prevent or hinder the formation of monodisperse bubbles below a certain diameter threshold. To overcome this problem, the bubble formation channel 130 may be fitted with one or more dispersed phase fluid jet stabilization provisions to stabilize the jet 32 in the downstream direction, so as to allow it to thin further and enable the formation of smaller bubbles 36.

Figure 3A:
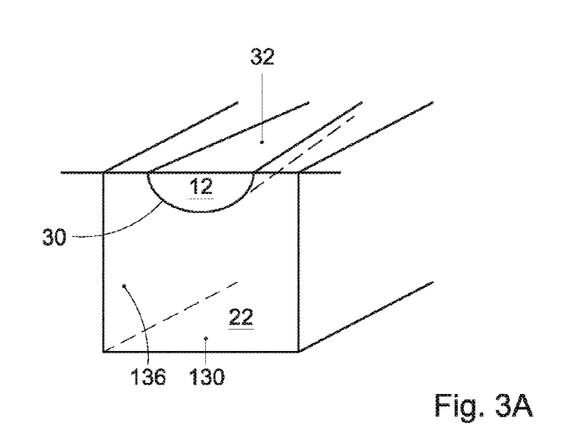
FIG. 3A-D shows four alternative schematic cross-sectional views of the bubble formation channel of the microfluidic flow focusing device of the apparatus shown in FIGS. 1 and 2.
Figure 3B:
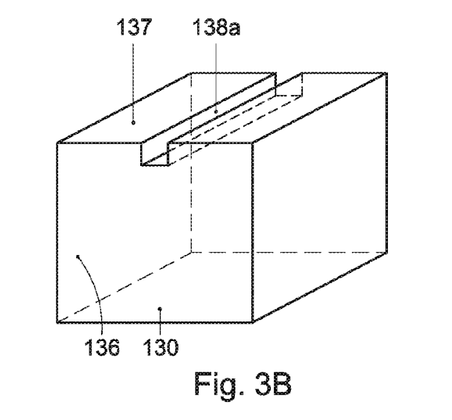
Figure 3C:
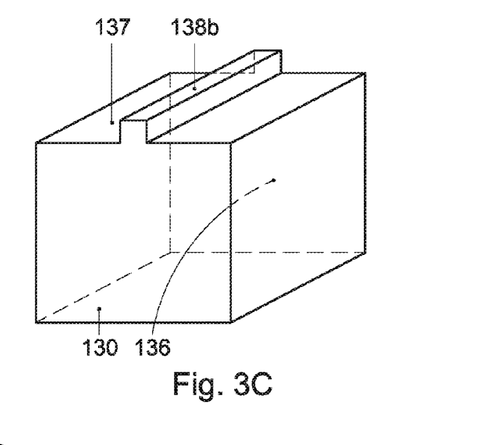
Figure 3D:
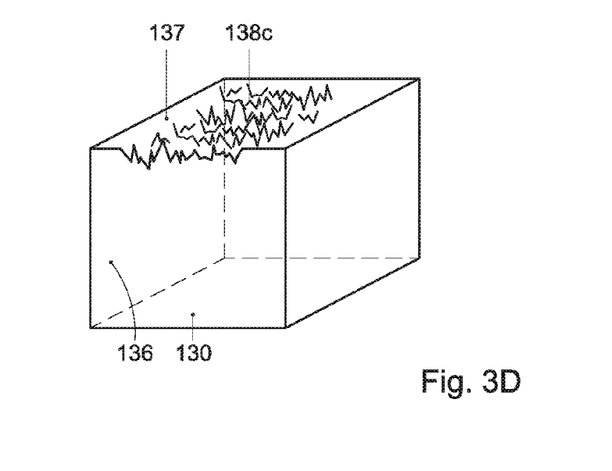

FIGS. 3A-D schematically illustrate four cross-sectional perspective views of the bubble formation channel 130. FIG. 3A illustrates the bubble formation channel 130 without any particular dispersed phase fluid jet stabilization provision, and during operation. FIGS. 3B-D schematically illustrate three alternative embodiments of the bubble formation channel 130 including dispersed phase fluid jet stabilization provisions. In all embodiments, the bubble formation channel 130 has a rectangular cross-section, such that the inner surface of the channel wall 136 defines four flat, longitudinally extending faces.

FIG. 3A schematically shows how, during operation, a wobbly dispersed phase fluid jet 32 extends into the bubble formation channel 130. The jet 32 is shown to adhere to the upper face 137 of the channel wall 136, but without particular stabilization provisions the choice for any face is essentially arbitrary. Where the jet 32 is not in contact with the upper face 137 of the channel wall 136, it is in contact with the co-flow of continuous phase fluid 22 that flanks and largely surrounds it.

To stabilize the jet 32 against the upper face 137 of the channel wall 136, the face may be manufactured from a material, possibly in the form of a coating, that possesses a low wettability with respect to the continuous phase fluid 22, or preferably at least a lower wettability than that provided by the materials from which the other faces are manufactured. For instance, in case the continuous phase fluid 22 is (distilled) water, the face 137 may be made of a (relatively) hydrophobic material. In general terms, the channel wall 136 of the bubble formation channel 130 may define a portion of inner surface area 137, such as a wall face in the case of prismatic channel, that extends substantially from the inlet 132 of the bubble formation channel 130 and in the longitudinal direction of that channel, and that has a low wettability with respect to the continuous phase fluid 22, or at least a lower wettability than adjacent inner surface area portions defined by the wall. The portion of surface area 137 need not extend of over the entire length $L_{bfc}$ of the bubble formation channel 130, but preferably over a distance of at least several tens of micrometers. The term 'low wettability' of a surface may be construed in terms of the contact angle of a droplet of continuous phase fluid on the respective surface; for a surface of low wettability, the contact angle may be ≥90°, preferably ≥110°, and more preferably ≥130°.

Alternatively or in addition to manufacturing the upper face 137 of a material with an absolute or relative low wettability, the upper face 137 of the channel wall 136 may be provided with a longitudinally extending surface enlarging provision. FIGS. 3B-D schematically illustrate, by way of example, how the upper surface 137, and more generally any longitudinally extending inner surface portion of the wall 136 defining the bubble formation channel 130, may be provided with a surface enlarging provision in the form of a longitudinally extending rim or ridge 138a, a longitudinally extending slot or groove 138b, and a roughened inner wall surface area 138c (e.g. surface area defined by nanopillars), respectively. A ridge 138a or groove 138b may preferably have transverse dimensions, e.g. width and depth, that are on the order of the diameter of bubbles 36 to be formed, i.e. 1-10 μm. The inner surface enlarging provision need not extend over the entire length $L_{bfc}$ of the bubble formation channel 130, but preferably over a distance of at least several tens of micrometers, and substantially from the inlet 132 on.

The outlet 134 of the bubble formation channel 130 may discharge into a bubble harvesting reservoir 160, 260, from which the bubbles 36 may be collected or harvested. The sudden release of a monodisperse microbubbles carrying flow of continuous phase fluid 22 from a bubble formation channel 130 into a reservoir 160 with relatively large dimensions, however, may cause (heavy) swirling of the continuous phase fluid 22, which may in turn cause the microbubbles 36 to coalesce. As a result, the microbubbles 36 may loose their monodispersity. To prevent such coalescence of bubbles 36, the outlet 134 of the bubble formation channel 130 may preferably be fluidly connected to the bubble harvesting reservoir 160, 260 via a transition channel 150 that is characterized by a design that prevents the bubbles 36 from being subjected to high shear rates, and hence a geometry/hydraulic diameter that varies only gradually, avoiding, for instance sudden expansions or constrictions. In the depicted embodiment, the planar transition channel 150 has essentially the shape of a truncated triangle with an apex angle 2θ, wherein θ=30°. For such truncated triangle-shaped transition channels 150, θ may preferably satisfy the condition θ≤45°, and more preferably θ≤30°. The condition is, of course, mutatis mutandis applicable to non-planar truncated cone-shaped transition channels.

It will be clear that the microfluidic flow focusing device 2 described above exhibits an essentially planar geometry in which the relevant channels 110, 120, 120', 130, and 150 are all disposed in a same plane. Although such planar geometry is advantageous from the point of manufacture, it is noted that the apparatus and method according to the present invention are not limited to planar flow focusing geometry. The apparatus and method may in particular also employ an axisymmetric, generally cylindrical (as opposed to planar) flow geometry; one embodiment with such a geometry would, for example, be obtained by revolving the above-described microfluidic flow focusing device 2 around the central axis A of the dispersed phase fluid supply channel 110.

An advantage of the depicted planar flow focusing device 2 is that it may be manufactured very economically. The base body 100, including the channel arrangement 100, 120, 120', 130, may for example be produced by soft lithography or photolithography techniques. The cover body 200, which may typically include only macroscopic structures 212, 222, 260, may be manufactured through conventional machining.

To supply the microfluidic flow focusing device 2 with fluids to run it, the apparatus 1 may include a dispersed phase fluid source 10, and a continuous phase fluid source 20. The dispersed phase fluid source 10 may supply pressurized dispersed phase fluid 12, which, in the context of flow focusing and bubble generation, may also be referred to as the core fluid or the focused fluid. The continuous phase fluid source 20 may supply pressurized continuous phase fluid 22, which, may also be referred to as the sheath fluid or focusing fluid. The sources 10, 20 may be any suitable source device for the chosen fluid, e.g. a pressurized vessel, a syringe pump, etc., and may include suitable regulators to enable control over the pressure and/or flow rate at which a respective fluid is supplied. The dispersed phase fluid source 10 may be fluidly connected to the inlet 112 of the dispersed phase fluid supply channel 110, in particular via the passage 212 in the cover body 200. Similarly, the continuous phase fluid source 20 may be fluidly connected to the inlet 122 of the continuous phase fluid supply channels 120, 120', in particular via the passage 222 in the cover body 200.

In case the dispersed phase fluid 12 is a gas, the continuous phase fluid 22 may be a liquid. The dispersed phase fluid 12 may, for example, include (biocompatible) gases such as air, nitrogen, oxygen, carbon dioxide, noble or inert gases, and fluorinated gases (e.g. $C_3F_8$, $C_4F_{10}$, $C_5F_{12}$); the continuous phase fluid may, for instance, be distilled water. Alternatively, in case the dispersed phase fluid 12 is a liquid, the continuous phase fluid 22 may be a gas.

In a preferred embodiment, at least one of the dispersed phase fluid 12 and the continuous phase fluid 22 may contain a surfactant suitable to populate a fluid interface 30 between the dispersed phase fluid 12 and the continuous phase fluid 22, and to thus encapsulate and stabilize bubbles 36 of dispersed phase fluid 12 within the continuous phase fluid 22 immediately upon formation. The surfactant may, for example, include a film-forming (mixture of) phospholipid(s), e.g. a mixture of DPPC, DPPA, and DPPE-PEG5000.

Now that the construction of the apparatus 1 according to the present invention has been described in some detail, attention is invited to its operation.

FIG. 4 schematically illustrates a top view of the microfluidic flow focusing device 2, and more specifically of a portion thereof including the flow focusing junction 140, during operation. The source of dispersed phase fluid 10, operably connected to the inlet 112 of the dispersed phase fluid supply channel 110, may force a flow of dispersed phase fluid 12 through the channel and into the junction 140 at a flow rate $Q_{dpf}$. Simultaneously, the source of continuous phase fluid 20, operably connected to the inlet 122 of the continuous phase fluid supply channels 120, 120', may force a flow of continuous phase fluid 22 through each of the two channels at a respective flow rate $Q_{cpf}/2$. Accordingly, continuous phase fluid 22 may be discharged into the flow focusing junction 140 at an overall flow rate $Q_{cpf}$. The flow rates $Q_{dpf}$ and $Q_{cpf}$ may satisfy the condition $Q_{dpf}/Q_{cpf} \ll 1$. In addition the overall configuration, including in particular the channel geometry of the flow focusing device 2 and the choice of fluids, may be such that the dimensionless Reynolds number Re and the dimensionless Weber number We of the flow of continuous phase fluid 22 within the bubble formation channel 130 satisfy the conditions $Re \geq 10^2$ and $We > 1$. Here, the Reynolds number Re may be defined as $Re = \rho \upsilon \omega / \mu$, wherein $\rho$ denotes the density of the continuous phase fluid 22, $\upsilon$ denotes the mean velocity of the continuous phase fluid 22, $\omega$ denotes the transversal dimension or hydraulic diameter of the bubble formation channel 130, and $\mu$ denotes the viscosity of the continuous phase fluid 22. The Weber number We may be defined as $We = \rho \upsilon^2 \omega / \sigma$, wherein $\rho$, $\upsilon$, and $\omega$ denote the same quantities as in the Reynolds number, and $\sigma$ denotes the surface tension coefficient.

As is apparent from FIG. 4, the flows of continuous phase fluid 22 engage the flow of dispersed phase fluid 12 in co-flow at the flow focusing junction 140. The flows of continuous phase fluid 22 thereby mould the interface between the dispersed phase fluid 12 and the continuous phase fluid 22 into a cusp that, under the influence of a relatively large pressure gradient, may give rise to a gradually thinning jet 32 of dispersed phase fluid 12 that extends into the inlet 132 of the bubble formation channel 130. A cross-sectional area of the jet 32 may be significantly smaller than a cross-sectional area of the bubble formation channel 130, preferably at least a factor five. Within the bubble formation channel 130, the laminar flow of continuous phase fluid 22 may develop a parabolic velocity profile. In this respect, it is noted that the configuration of the flow focusing device 2 in combination with the operational parameters that define its use (in particular the flow rates $Q_{dpf}$ and $Q_{cpf}$) may preferably be chosen to maximize the aforementioned pressure gradient in the direction of the flow at the inlet 132 of the bubble formation channel 130. The relatively large pressure gradient helps to ensure proper development of the continuous phase fluid 22 from a flat velocity profile at the inlet 132 to a parabolic velocity profile further downstream. A centerline of the parabolic velocity profile may substantially coincide with a centerline of the jet 32, such that the jet 32 is effective stretched thinner as it extends further into the bubble formation channel 130. As the jet 32 is inherently unstable, bubbles 36 may spontaneously pinch off or break off its tip 34.

The point at which the bubbles 36 pinch off may be dependent on the presence of the aforementioned jet stabilization provisions, such as the inner wall surface portion 137 of low wettability and/or the inner wall surface enlarging provisions 138a-c (e.g. rim, groove, roughened surface area). As discussed, these features may prevent early break up of the jet 32 at its tip 34 and enable further thinning thereof in the flow direction, such that it may develop into an elongate, thin thread from which, eventually, even smaller bubbles may pinch off.

In case either one of the dispersed phase fluid 12 and the continuous phase fluid 22 contains a suitable surfactant, the surfactant molecules may spontaneously populate the dispersed phase fluid-continuous phase fluid interfaces of the bubbles 36 upon their formation, and thus encapsulate and stabilize them against dissolution. The bubbles 36 may then be carried along in the flow of continuous phase fluid 22 towards the bubble harvesting reservoir 160, 260. In preparation of discharge into the (relatively large) reservoir 160, 260, the bubbles 36 may preferably pass through a transition channel 150 with a slowly/gradually increasing hydraulic diameter to prevent the bubbles 36 from being subjected to high shear rates that might damage them and/or cause their coalescence. Once the bubbles 36 are discharged into the bubble harvesting reservoir 160, 260, they may easily be harvested, e.g. by sucking up desired amounts of bubble-comprising continuous phase fluid 22 and bottling them, optionally after evaporating at least part of the continuous phase fluid 22.

Microbubble generation experiments carried out by the inventors of the present invention, using an apparatus and method identical or in some respects similar to the embodiments of the invention discussed above, are described in detail in E. Castro-Hernández, W. Van Hoeve, D. Lohse, J. M. Gordillo, *Microbubble generation in a co-flow device operated in a new regime*, Lab on a Chip, 2011, 11, 2023-2029, which publication is hereby incorporated by reference in its entirety.

With regard to the terminology used in this text and not elaborated on above, the following may be noted. The term 'bubble' may be construed to refer to a typically globular body of a first fluid (the dispersed phase), disposed within a second fluid (the continuous phase). In case the first fluid is a gas, the second fluid may be a liquid. In case the first fluid is liquid, the second fluid may be a gas; the body of the first fluid may then also be referred to as a 'droplet'. The term 'channel' may be construed to refer to a microchannel, i.e. a channel having a hydraulic diameter that is preferably smaller than 1 mm, or at least smaller than 10 mm. The mathematical symbols "<<" and ">>" may be construed to mean 'much smaller than' and 'much greater than', respectively. More precisely, the symbols may indicate a difference factor of at least ten; i.e. the mathematical expression "a>>b" may be construed to mean that a is at least ten times greater than b, or: "a≥10·b". The 'hydraulic diameter' of a channel may be defined as 4·A/P, wherein A denotes the cross-sectional area of the channel, and P the wetted perimeter of the cross-section. For a channel with a circular cross-section, the hydraulic diameter simply amounts to the diameter of the channel; for a channel with a square cross-section, the hydraulic diameter amounts to the side length of the square.

Although illustrative embodiments of the present invention have been described above, in part with reference to the accompanying drawings, it is to be understood that the invention is not limited to these embodiments. Variations to the disclosed embodiments can be understood and effected by those skilled in the art in practicing the claimed invention, from a study of the drawings, the disclosure, and the appended claims. Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, it is noted that particular features, structures, or characteristics of one or more embodiments may be combined in any suitable manner to form new, not explicitly described embodiments.

LIST OF ELEMENTS 1 apparatus
2 flow focusing device
10 source of dispersed phase fluid
12 dispersed phase fluid
20 source of continuous phase fluid
22 continuous phase fluid
30 interface between dispersed phase fluid and continuous phase fluid
32 jet of dispersed phase fluid
34 tip of jet
36 microbubble
100 base body
102 main (top) surface of base body
110 dispersed phase fluid supply channel
112 inlet of dispersed phase fluid supply channel
114 outlet of dispersed phase fluid supply channel
120 continuous phase fluid supply channel
122 inlet of continuous phase fluid supply channel
124 outlet of continuous phase fluid supply channel
126 tapering portion of continuous phase fluid supply channel
128 cross-channel
130 bubble formation channel
132 inlet of bubble formation channel
134 outlet of bubble formation channel
136 channel wall
137 face of low wettability
138a ridge
138b groove
138c roughened inner wall surface area
140 flow focusing junction
150 transition channel
160 bubble harvesting reservoir (bottom portion)
200 cover body
202 main (top) surface of cover body
204 main (bottom) surface of cover body
212 passage for dispersed phase fluid
222 passage for continuous phase fluid
260 bubble harvesting reservoir (top portion)
A central axis of dispersed phase fluid supply channel
$D_{bfc}$ hydraulic diameter of bubble formation channel
$D_{cpfsc}$ hydraulic diameter of continuous phase fluid supply channel
$D_{cpfsc,outlet}$ hydraulic diameter of continuous phase fluid supply channel outlet
$d_b$ (average) bubble diameter
$I_{dpf}$ dispersed phase fluid jet direction
$I_{cpf}$, $I_{cpf}'$ continuous phase fluid discharge direction
$L_{bfc}$ length of bubble formation channel
$Q_{dpf}$ flow rate of dispersed phase fluid
$Q_{cpf}$ flow rate of continuous phase fluid
$\omega_{bfc}$ width of bubble formation channel
δ angle of tapering portion of continuous phase fluid supply channel
φ wall angle at inlet of bubble formation channel
θ angle of widening transition channel

What is claimed is:

1. A method of mass producing monodisperse microbubbles, the method comprising:
providing an apparatus comprising at least one microfluidic flow focusing device comprising a dispersed phase fluid supply channel having an outlet that discharges into a flow focusing junction, at least one continuous phase fluid supply channel having an outlet that discharges into the flow focusing junction, and a bubble formation channel having an inlet disposed at the flow focusing junction; and
supplying a flow of dispersed phase fluid through the outlet of the dispersed phase fluid supply channel into the flow focusing junction, and supplying a flow of continuous phase fluid through the outlet of the at least one continuous phase fluid supply channel into the flow focusing junction,
such that, at the junction, the flow of dispersed phase fluid is engaged in co-flow by the focusing flow of continuous phase fluid under formation of a gradually thinning jet of dispersed phase fluid that extends into the inlet of the bubble formation channel, and monodisperse microbubbles, having a diameter smaller than the hydraulic diameter of the bubble formation channel break off a tip of said jet, wherein said bubble formation channel has a length that is much greater than its hydraulic diameter by a factor of at least ten.

2. The method according to claim 1, wherein the diameter of the monodisperse microbubbles, $d_b$, satisfies the condition $d_b \leq 10$ μm, and preferably 2 μm$\leq d_b \leq$5 μm.

3. The method according to claim 1, wherein $Q_{dpf}/Q_{cpf} \ll 1$, and conditions within the bubble formation channel are such that $Re \geq 10^2$, and $We > 1$, wherein Re denotes a Reynolds number of the continuous phase fluid in the bubble formation channel;
wherein We denotes a Weber number of the continuous phase fluid in the bubble formation channel;
wherein Qdpf denotes a flow rate of the imposed dispersed phase fluid through the dispersed phase fluid supply channel; and
wherein Qcpf denotes a flow rate of the imposed continuous phase fluid through the at least one continuous phase fluid supply channel.

4. The method according to claim 1, wherein at least $10^5$ monodisperse microbubbles break off of the tip of the jet per second.

5. An agent comprising a plurality of monodisperse microbubbles manufactured through the method according to claim 1.

6. The method according to claim 1, wherein at least one of the dispersed phase fluid and the continuous phase fluid contains a surfactant suitable to populate a fluid interface between the dispersed phase fluid and the continuous phase fluid, and to thus stabilize bubbles of dispersed phase fluid within the continuous phase fluid.

7. The method according to claim 1, wherein the bubble formation channel is bounded by a wall having a portion of inner wall surface that extends substantially from the inlet of the bubble formation channel and in a longitudinal direction thereof, and that has a low wettability with respect to the continuous phase fluid.

8. The method according to claim 1, wherein the bubble formation channel is bounded by a wall having a portion of inner wall surface that extends substantially from the inlet of the bubble formation channel and in a longitudinal direction thereof, and that defines an inner wall surface enlarging provision.

9. The method according to claim 8, wherein the inner wall surface enlarging provision includes at least one of a longitudinally extending ridge, a longitudinally extending slot, and a roughened inner wall surface area.

10. The method according to claim 8, wherein said portion of inner wall surface with low wettability defines said inner wall surface enlarging provision.

11. The method according to claim 1, wherein bubble formation channel is substantially straight and substantially uniform in cross-section over its length $L_{bfc}$.

12. The method according to claim 1, wherein the length of the bubble formation channel $L_{bfc} > 1$ mm.

13. The method according to claim 1, wherein the hydraulic diameter $D_{bfc}$ of the bubble formation channel satisfies the condition 10 μm$<D_{bfc}<$100 μm.

14. The method according to claim 1, wherein the apparatus further comprises:
a bubble harvesting reservoir;
a transition channel, wherein said transition channel fluidly connects an outlet of the bubble formation channel to the bubble harvesting reservoir, and wherein said transition channel has a gradually increasing hydraulic diameter.

15. The method according to claim 1, wherein the at least one microfluidic flow focusing device has a substantially planar flow focusing geometry, such that the respective channels at least partially extend in a same plane.

16. The method according to claim 1, wherein the at least one microfluidic flow focusing device includes two continuous phase fluid supply channels,
wherein the outlet the dispersed phase fluid supply channel, the outlets of the two continuous phase fluid supply channels, and the inlet of the bubble formation channel define the flow focusing junction,
wherein the dispersed phase fluid supply channel is substantially aligned with the bubble formation channel, such that the inlet of the bubble formation channel is disposed opposite the outlet of the dispersed phase fluid supply channel, and
wherein the outlets of the two continuous phase fluid channels join the flow focusing junction from substantially opposite sides.

17. The method according to claim 16, wherein the continuous phase fluid supply channels include a tapering portion just upstream of their respective outlets.

18. The method according to claim 1, wherein the dispersed phase fluid is a gas and the continuous phase fluid is a liquid.

19. The method according to claim 18, wherein the length of the bubble formation channel is such that the flow of continuous phase fluid through the bubble formation channel is enabled to develop an at least approximately parabolic velocity profile.

20. The method according to claim 19, wherein a centerline of the parabolic velocity profile substantially coincides with a centerline of the jet, such that the jet is effectively stretched thinner as it extends further into the bubble formation channel.

21. The method according to claim 20, wherein the monodisperse microbubbles break off the tip of the jet to form while still inside an initial part of the length of the bubble formation channel, wherein the monodisperse microbubbles continue to travel along at least some remaining part of the length of the bubble formation channel.

* * * * *